(12) United States Patent
Okamura et al.

(10) Patent No.: US 8,700,123 B2
(45) Date of Patent: Apr. 15, 2014

(54) ENVIRONMENT PROPERTY ESTIMATON AND GRAPHICAL DISPLAY

(75) Inventors: Allison Mariko Okamura, Towson, MD (US); Tomonori Yamamoto, Baltimore, MD (US); Peter Balazs Vagvolgyi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 391 days.

(21) Appl. No.: 13/124,350

(22) PCT Filed: Oct. 20, 2009

(86) PCT No.: PCT/US2009/061297
§ 371 (c)(1),
(2), (4) Date: Apr. 14, 2011

(87) PCT Pub. No.: WO2010/048160
PCT Pub. Date: Apr. 29, 2010

(65) Prior Publication Data
US 2011/0201885 A1  Aug. 18, 2011

Related U.S. Application Data

(60) Provisional application No. 61/106,683, filed on Oct. 20, 2008.

(51) Int. Cl.
*A61B 5/00* (2006.01)
(52) U.S. Cl.
USPC .......................................... 600/407; 600/476
(58) Field of Classification Search
USPC .................................................. 600/407, 476
See application file for complete search history.

(56) References Cited

U.S. PATENT DOCUMENTS

| 5,855,553 | A | 1/1999 | Tajima et al. |
| 6,165,128 | A | 12/2000 | Cespedes et al. |
| 6,585,647 | B1 | 7/2003 | Winder |
| 6,758,815 | B2 | 7/2004 | Bernardi |
| 2006/0020213 | A1 | 1/2006 | Whitman et al. |
| 2006/0052702 | A1 | 3/2006 | Matsumura et al. |
| 2007/0083098 | A1 | 4/2007 | Stern et al. |
| 2008/0074689 | A1 | 3/2008 | Yamada et al. |

FOREIGN PATENT DOCUMENTS

| JP | H08215211 A | 8/1996 |
| JP | 2008134373 A | 6/2008 |

OTHER PUBLICATIONS

Althoefer et al., "Air-cushion force sensitive probe for soft tissue investigation during minimally invasive surgery," in *IEEE Conference on Sensors*, pp. 827-830, 2008.

(Continued)

*Primary Examiner* — Peter Luong
(74) *Attorney, Agent, or Firm* — Venable LLP; Henry J. Daley

(57) ABSTRACT

A surgical robot including an imaging system comprising at least one camera, a processor in communication with the imaging system, a manipulation system in communication with the processor, and a visual display in communication with the processor. The processor is operable to calculate a stiffness estimate for an area of an environment based on an environment model of tool-environment interaction data, create a composite image comprising a stiffness map of the stiffness estimate overlaid on an environment image from the at least one camera, and output the composite image on the visual display.

28 Claims, 8 Drawing Sheets

(56) References Cited

OTHER PUBLICATIONS

Colton et al., "Identification of nonlinear passive devices for haptic simulations," in WHC '05: Proceedings of the First Joint Eurohaptics Conference and Symposium on Haptic Interfaces for Virtual Environment and Teleoperator Systems, (Washington, DC, USA), pp. 363-368, IEEE Computer Society, 2005.

Corteso et al., "Haptic control design for robotic-assisted minimally invasive surgery," *IEEE International Conference on Intelligent Robots and Systems*, pp. 454-459,Oct. 9-15, 2006.

Corteso et al., "Real-time adaptive control for haptic telemanipulation with kalman active observers," *IEEE Transactions on Robotics*, vol. 22, No. 5, pp. 987-999, 2006.

Dargahi et al., "Graphical display of tactile sensing data with application in minimally invasive surgery," Canadian Journal of Electrical and Computer Engineering, vol. 32, No. 3, pp. 151-155, 2007.

Diolaiti et al., "Contact impedance estimation for robotic systems," *IEEE Transactions on Robotics*, vol. 21, No. 5, pp. 925-935, Oct. 2005.

Erickson et al., "Contact stiffness and damping estimation for robotic systems," *The International Journal of Robotics Research*, vol. 22, No. 1, pp. 41-57, Jan. 2003.

Hacksel et al., "Estimation of environment forces and rigid-body velocities using observers," in *IEEE International Conference on Robotics and Automation*, pp. 931-936, 1994.

Hashtrudi-Zaad et al., "Adaptive transparent impedance reflecting teleoperation," in *IEEE International Conference on Robotics and Automation*, pp. 1369-1374, Apr. 1996.

Hoyt et al., "Tissue elasticity properties as biomarkers for prostate cancer", *Cancer Biomark*, 4(4-5):213-225, 2008.

Hunt et al., "Coefficient of restitution interpreted as damping in vibroimpact," *ASME Journal of Applied Mechanics*, vol. 42, No. 2, pp. 440-445, Jun. 1975.

Kaneko et al., "Active strobe imager for visualizing dynamic behavior of tumors," in *IEEE International Conference on Robotics and Automation*, pp. 3009-3014, Apr. 10-14, 2007.

Leven et al., "Davinci canvas: A telerobotic surgical system with integrated, robot-assisted, laparoscopic ultrasound capability," in *Medical Image Computing and Computer-Assisted Intervention (MICCAI)*, pp. 811-818, 2005.

Love et al., "Environment estimation for enhanced impedance control," in *IEEE International Conference on Robotics and Automation*, pp. 1854-1858, 1995.

Mahvash et al., "Enhancing transparency of a position-exchange teleoperator," in Second Joint Eurohaptics Conference and Symposium on Haptic Interfaces for Virtual Environment and Teleoperator Systems (World Haptics), pp. 470-475, 2007.

Mahvash et al., "Force-Feedback Surgical Teleoperator: Controller Design and Palpation Experiments", *16th Symposium on Haptic Interfaces for Virtual Environments and Teleoperator Systems*, pp. 465-471, Reno, NV, Mar. 2008.

Mayer et al., "Haptic feedback in a telepresence system for endoscopic heart surgery," *Presence: Teleoperators and Virtual Environments*, vol. 16, No. 5, pp. 459-470, Oct. 2007.

Miller et al., "Tactile imaging system for localizing lung nodules during video assisted thoracoscopic surgery," in *IEEE International Conference on Robotics and Automation*, pp. 2996-3001, Apr. 10-17, 2007.

Misra et al., "Environment parameter estimation during bilateral telemanipulation," in *14th Symposium on Haptic Interfaces for Virtual Environments and Teleoperator Systems*, pp. 301-307, Mar. 25-26, 2006.

Misra et at "Modeling of tool-tissue interactions for computer-based surgical simulation: A literature review," *Presence: Teleoperators and Virtual Environments*, vol. 17, No. 5, pp. 463-491, Oct. 2008.

Mohr et al., "Computer-enhanced 'robotic'-cardiac surgery: experience in 148 patients," *The Journal of Thoracic and Cardiovascular Surgery*, vol. 121, No. 5, pp. 842-853, 2001.

Okamura, "Haptic feedback in robot-assisted minimally invasive surgery," *Current Opinion in Urology*, vol. 19, No. 1, pp. 102-107, Jan. 2009.

Singh et al., "An analysis of some fundamental problems in adaptive control of force and impedance behavior: Theory and experiments," IEEE Transactions on Robotics and Automation, vol. 11, No. 6, pp. 912-921, Dec. 1995.

Trejos et al., "Experimental evaluation of robot-assisted tactile sensing for minimally invasive surgery," in *IEEE International Conference on Biomedical Robotics and Biomechatronics*, pp. 971-976, 2008.

Wang et al., "Design of bilateral teleoperators for soft environments with adaptive environmental impedance estimation," in *IEEE International Conference on Robotics and Automation*, pp. 1127-1132, Apr. 2005.

Wellman et al., "Tactile imaging of breast masses first clinical report," *Archives of Surgery*, vol. 136, pp. 204-208, Feb. 2001.

Yamamoto et al., "Techniques for Environment parameter Estimation During Telemanipulation," in *IEEE International Conference on Biomedical Robotics and Biomechatronics*, pp. 217-223, Oct. 19-22, 2008.

Reiley et al., "Effects of visual force feedback on robot-assisted surgical task performance", *The Journal of Thoracic and Cardiovascular Surgery*, Jan. 2008, vol. 135, No. 1, pp. 196-202.

Tsuchimoto et al., "Augmented-Reality Visualization of Tissue Stiffness Data", Proceedings of the International Conference on Medical Information Visualisation—Biomedical Visualisation, 2006, 6 pages.

International Search Report and Written Opinion for PCT/US2009/061297.

International Search Report and Written Opinion for PCT/US2009/061297, Dated 2009.

Okamura et al., "Haptics for robot-assisted minimally invasive surgery," in *Proceedings of the International Symposium Robotics Research*, Hiroshima, Japan, Nov. 26-29, 2007.

Ophir et al., "Elastography: Imaging the elastic properties of soft tissues with ultrasound," in *Journal of Medical Ultrasonics*, vol. 29, pp. 155-171, 2002.

Seraji et al., "Force tracking in impedance control," *IEEE Transactions on Robotics*, vol. 16, No. 1, pp. 97-117, 1997.

Srinivasan et al., "Tactual Discrimination of Softness," *Journal of Neurology*, 1995, vol. 73, pp. 88-101.

Translation of Office Action issued in Japanese Patent Application No. 2011-532328 dated Nov. 12, 2013.

ENVIRONMENT PROPERTY ESTIMATON AND GRAPHICAL DISPLAY

CROSS-REFERENCE TO RELATED APPLICATION

This application claims priority to U.S. Provisional Application No. 61/106,683 filed Oct. 20, 2008, the entire contents of which are hereby incorporated by reference, and is a U.S. national stage application under 35 U.S.C. §371 of PCT/US2009/061297, filed Oct. 20, 2009, the entire contents of which are incorporated herein by reference.

The U.S. Government has a paid-up license in this invention and the right in limited circumstances to require the patent owner to license others on reasonable terms as provided for by the terms of Grant Nos. IIS-0347464, EEC-9731748 and CNS-0722943, awarded by the National Science Foundation, and of Grant No. R01-EB002004, awarded by the National Institutes of Health.

BACKGROUND

1. Field of Invention

The current invention relates to environment property estimation and graphical display, and more particularly to a surgical robot operable to graphically display environment property estimates.

2. Discussion of Related Art

The contents of all references, including articles, published patent applications and patents referred to anywhere in this specification are hereby incorporated by reference.

A teleoperated robot-assisted surgical system such as the da Vinci (Intuitive Surgical Inc., Sunnyvale, Calif., USA) provides a number of advantages over conventional minimally invasive surgery (MIS). It enhances dexterity, enables more precise motions, and provides 3-dimensional (3D) visualization. However, the lack of haptic feedback has been recognized as one of the drawbacks of such teleoperated robot-assisted minimally invasive surgery (RMIS) systems (F. W. Mohr, V. Falk, A. Diegeler, T. Walther, J. F. Gummert, J. Bucerius, S. Jacobs, and R. Autschbach, "Computer-enhanced 'robotic' cardiac surgery: experience in 148 patients," *The Journal of Thoracic and Cardiovascular Surgery*, vol. 121, no. 5, pp. 842-853, 2001). Although many research groups, e.g. M. Mahvash, J. Gwilliam, R. Agarwal, B. Vagvolgyi, L.-M. Su, D. D. Yuh, and A. M. Okamura, "Force-feedback surgical teleoperator: Controller design and palpation experiments," in 16*th Symposium on Haptic Interfaces for Virtual Environments and Teleoperator Systems*, pp. 465-471, 2008, H. Mayer, I. Nagy, A. Knoll, E. U. Braun, R. Bauernschmitt, and R. Lange, "Haptic feedback in a telepresence system for endoscopic heart surgery,"*Presence: Teleoperators and Virtual Environments*, vol. 16, no. 5, pp. 459-470, 2007, and M. Tavakoli, R. Patel, M. Moallem, and A. Aziminejad, *Haptics for Teleoperated Surgical Robotic Systems* (New Frontiers in Robotics series), World Scientific Publishing Company, 2008, have studied teleoperation with haptic feedback for surgical applications, the trade-off between stability and transparency, and force sensor issues such as cost, biocompatibility, and sterilizability, make it difficult to develop a practical system (based on current commercially available surgical robots) with realistic haptic feedback (A. M. Okamura, L. N. Verner, C. E. Reiley, and M. Mahvash, "Haptics for robot-assisted minimally invasive surgery," in *Proceedings of the International Symposium Robotics Research*, Hiroshima, Japan, Nov. 26-29, 2007) and (A. M. Okamura, "Haptic feedback in robot-assisted minimally invasive surgery," Current Opinion in Urology, vol. 19, no. 1, pp. 102-107, 2009). Thus, surgeons using current RMIS systems principally rely on visual cues such as tissue deformation to estimate how much force a remote tool is applying to tissue.

During a procedure, surgeons often manually palpate biological tissues to investigate anatomical structures. Palpation provides both force-displacement and distributed tactile information. Tissue abnormalities can be differentiated from normal tissue by their mechanical properties, such as stiffness (e.g., K. Hoyt, B. Castaneda, M. Zhang, P. Nigwekar, P. A. di Sant'agnese, J. V. Joseph, J. Strang, D. J. Rubens, and K. J. Parker. Tissue elasticity properties as biomarkers for prostate cancer. *Cancer Biomark*, 4(4-5):213-225, 2008. Neurophys, 73:88, 1995). In coronary artery bypass grafting surgery (CABG), palpation is especially beneficial in detecting where to place grafts. It is better to graft soft undiseased arteries that are difficult to differentiate visually from calcified arteries. Grafts should not be placed adjacent to or directly onto a calcified artery segment. Without force feedback, finding the location of a calcified artery in heart tissue is quite challenging, and surgeons may be unable to determine the best location for anastomosis (F. W. Mohr, V. Falk, A. Diegeler, T. Walther, J. F. Gummert, J. Bucerius, S. Jacobs, and R. Autschbach, "Computer-enhanced 'robotic' cardiac surgery: experience in 148 patients," *The Journal of Thoracic and Cardiovascular Surgery*, vol. 121, no. 5, pp. 842-853, 2001).

There is thus a need for improved surgical robots, components, and methods for environment property estimation

SUMMARY

A surgical robot according to an embodiment of the current invention has an imaging system comprising at least one camera, a processor in communication with the imaging system, a manipulation system in communication with the processor, and a visual display in communication with the processor. The processor is operable to calculate a mechanical property, estimate for an area of an environment based on an environment model of tool-environment interaction data, create a composite image comprising a mechanical property map of the mechanical property estimate overlaid on an environment image from at least one camera, and output the composite image on the visual display.

A data processing unit for use with a surgical robot according to an embodiment of the current invention has at least one input port adapted to receive an environment image from the surgical robot and to receive tool-environment interaction data from the surgical robot, an overlay component in communication with the at least one input port, and an output port in communication with the overlay component. The overlay component is adapted to calculate a mechanical property estimate for an area of an environment based on an environment model of tool-environment interaction data, create a composite image comprising a map of the mechanical property overlaid on the environment image, and output the composite image to the output port.

A tangible machine readable storage medium that provides instructions, which when executed by a computing platform cause the computing platform to perform operations including a method including, according to an embodiment of the current invention, determining tool-environment interaction data from a palpation of an area of an environment, calculating a mechanical property estimate of the area of the environment based on the tool-environment interaction data, receiving an environment image, generating a composite image comprising a mechanical property map of the mechanical property estimate overlaid on the environment image, and outputting the composite image on a visual display.

BRIEF DESCRIPTION OF THE DRAWINGS

The invention may be better understood by reading the following detailed description with reference to the accompanying figures, in which.

DETAILED DESCRIPTION

Figure 1:
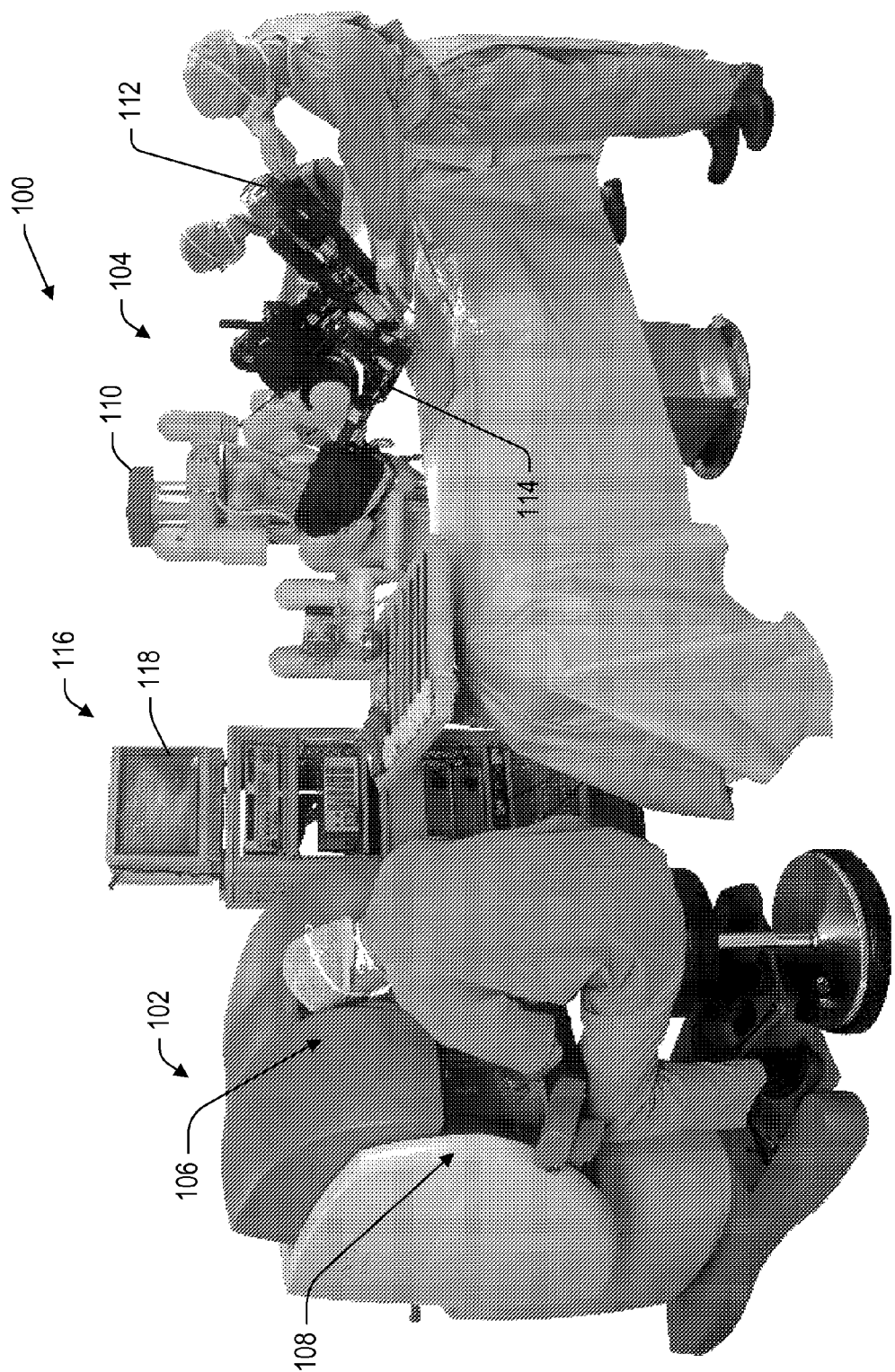
FIG. 1 is a schematic illustration of a surgical robot for tissue property estimation and graphical display according to an embodiment of the current invention.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

FIG. 1 is a schematic illustration of a surgical robot 100 for environment property estimation and graphical display according to an embodiment of the current invention. The surgical robot 100 includes a master console 102 and a patient-side manipulator 104. The master console 102 includes a visual display 106 and manipulator 108. The patient-side manipulator 104 includes a manipulation system 110. In an embodiment, the manipulation system 110 includes a manipulation tool 112 and an imaging system 114. In the embodiment, a surgical robot 100 includes an imaging system 114 including at least one camera, a processor 116 in communication with the imaging system 114, a manipulation system 110 in communication with the processor 116, and a visual display 106 in communication with the processor 116. The processor 116 calculates a mechanical property estimate for an area of an environment based on an environment model of tool-environment interaction data, creates a composite image comprising a mechanical property map of the mechanical property estimate overlaid on an environment image from the at least one camera, and outputs the composite image on the visual display 106.

In an embodiment, the mechanical property is a stiffness. The stiffness can be linear or nonlinear. In another embodiment, the mechanical property is linear or nonlinear damping. In another embodiment, the mechanical property is damping. In another embodiment, the mechanical property is any mechanical property that can be detected by the system, such as, e.g., but not limited to, stiffness, damping, or mass, etc.

In an embodiment, a user can utilize the surgical robot 100 to provide a composite image so the user can identify areas of the tissue abnormalities based on estimated stiffness of the tissue. The estimated stiffness is calculated using tool-environment interaction data from palpation of the tissue. The user manipulates the manipulators 108 of the master console 102 to manually control the surgical robot 100 to palpate the tissue area. Alternatively, the user selects the area of tissue to palpate, but the surgical robot 100 controls the palpation of the tissue area. In another embodiment, the surgical robot 100 automatically palpates the tissue including the tissue abnormality area.

To carry out palpation of the tissue area, the processor 116 of the surgical robot 100 instructs the manipulation system 110 to palpate an area of tissue with the manipulation tool 112. The processor 116 receives tool-environment interaction data for the interaction between the manipulation tool 112 and the tissue during the palpation.

The tool-environment interaction data include data for the position of the manipulation tool 112 when palpating the tissue area. The tool-environment interaction data can also include other data, such as, for example, velocity and acceleration of the manipulation tool 112, the force exerted by the manipulation tool 112 on the tissue, or the amount of displacement the manipulation tool 112 causes to the tissue. While the manipulation tool 112 is in contact with the tissue, many characteristics of the manipulation tool 112 also correspond to characteristics of the tissue. For example, while the manipulation tool 112 is in contact with the tissue, the change in position of the manipulation tool 112 corresponds to the change in position of the tissue.

The processor 116 can receive the tool-environment interaction data from a variety of sources. In an embodiment, the position of the manipulation tool 112 can be known by the processor 116 thorough position sensors in the manipulation system 110, or through analysis of the data from the imaging system 114. The processor 116 monitors the position of the manipulation tool 112 and calculates the velocity and acceleration of the manipulation tool based on changes in the position of the manipulation tool 112. Alternatively, the manipulation tool 112 includes velocity and acceleration sensors in communication with the processor 116. Determination of other tool-environment interaction data is further described below in regards to FIGS. 2A, 2B, and 2C.

During a single palpation, the processor 116 receives multiple sets of tool-environment interaction data. Based on the tool-environment interaction data, the processor 116 then calculates a stiffness estimate, representing an estimated stiffness, for the area of tissue palpated.

To calculate the stiffness estimate for the area of the tissue, the processor 116 uses a tissue model and applies the tool-environment interaction data to the tissue model to estimate the unknown parameters of the tissue model. Various tissue models can be used, such as, e.g., but not limited to, a Kelvin-Voigt model, a Mass-damper-spring model, a Hunt-Crossley model, a 2nd order polynomial model, a 3rd order polynomial model, a 4th order polynomial model, or a 2nd order polynomial and velocity-dependent model. Various types of estimation techniques for estimating the unknown parameters of the tissue model can also be used, such as, e.g., but not limited to, recursive least squares, adaptive identification, the Kalman filter, and signal processing. The processor 116 obtains the stiffness estimate from the estimated unknown parameters of the tissue model.

Using the stiffness estimate and the environment image from the imaging system 114, the processor 116 creates the composite image. The composite image includes a stiffness map of the stiffness estimate overlaid on an environment image from the at least one camera. The stiffness map is a graphical representation of the calculated stiffness estimate of one or more areas of the tissue, and is further described below in regards to FIG. 3.

The processor 116 creates the composite image such that the areas of the stiffness map correspond to the areas of the environment the stiffness map overlays in the environment image. Creating a composite image includes creating the stiffness map based on translation of the stiffness estimate to the environment image. The processor 116 analyzes the environment image to translate an area of the environment to an area of the environment image showing the area of the environment. Based on the translation, the processor 116 then creates the stiffness map and overlays the stiffness map on the environment image. The processor 116 overlays the stiffness map in a semi-transparent fashion so the underlying environment image is still visible in the composite image. The composite image is then output on the visual display 106. According to an embodiment, the processor 116 creates the composite image in real time.

The visual display 106 shows users the composite image. The visual display 106 is a stereo display. The visual display 106 shows a three dimensional stereo view to the user through two separate displays, one display for each eye. Each of the displays shows a different composite image corresponding to the viewpoint of the environment for that eye. In another embodiment, the visual display 106 is instead a non-stereo display 118.

Figure 2C:
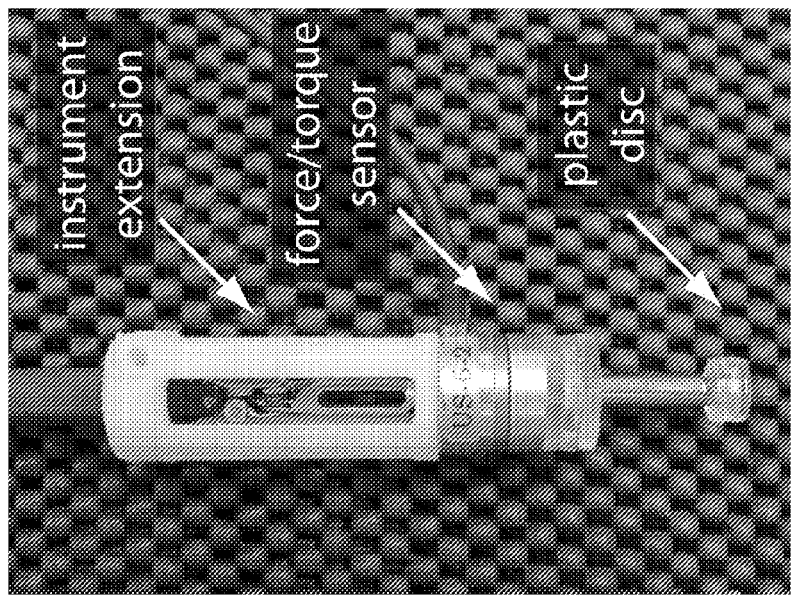
FIGS. 2A, 2B, and 2C are schematic illustrations of a palpation tool attachment according to an embodiment of the current invention.
Figure 2B:
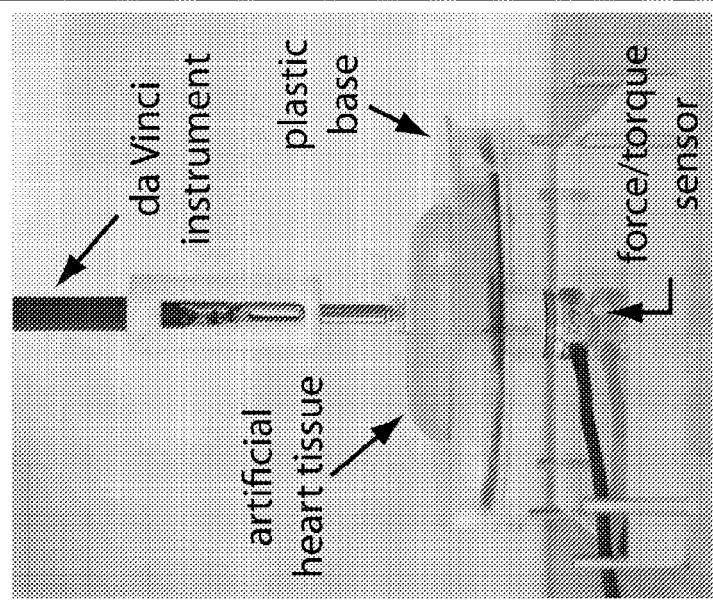
Figure 2A:
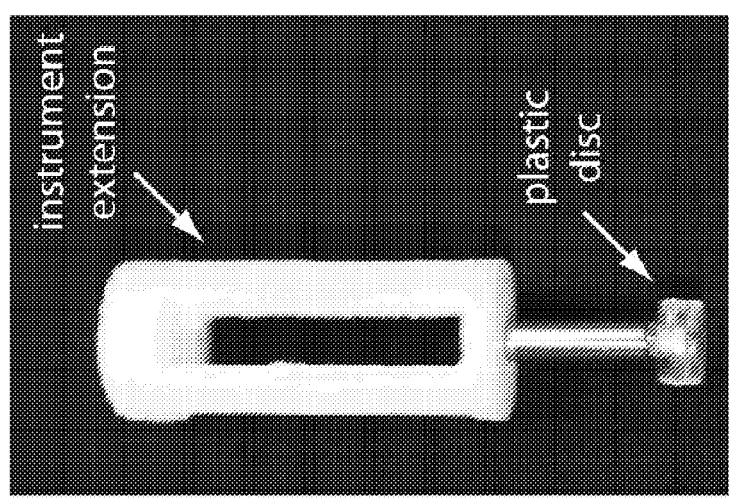

FIGS. 2A, 2B, and 2C are schematic illustrations of a palpation tool attachment according to an embodiment of the current invention. FIG. 2A depicts an embodiment of an attachment for the manipulation tool 112. The attachment includes an instrument extension component and a clear plastic disc. As shown in FIG. 2B, the instrument extension component is attached to the manipulation tool 112. Although in this embodiment, the clear plastic disc is the contact point for palpating the tissue, the disc can be made of any other suitable material and can be any other suitable shape. Additionally, instead of a separate attachment, the attachment can instead be incorporated into the manipulation tool 112.

As shown in FIG. 2C, in an embodiment, the manipulation tool 112 includes a tool-environment interaction sensor. The tool-environment interaction sensor is a force sensor. The manipulation tool 112 is arranged so the force sensor measures the force exerted on the environment by the manipulation tool 112. Based on changes in the force measured by the force sensor, the processor 116 can also determine the moment of contact and non-contact between the manipulation tool 112 and the environment. The tool-environment interaction data include the force measured by the force sensor and the processor 116 calculates the stiffness estimates based on the measured force and robot position.

In another embodiment, the tool-environment interaction force is not measured by a force sensor but instead estimated from the robot controller, following the method of M. Mahvash, J Gwilliam, R. Agarwal, B. Vagvolgyi, L. Su, D. D. Yuh, and A. M. Okamura, "Force-Feedback Surgical Teleoperator: Controller Design and Palpation Experiments", 16*th Symposium on Haptic Interfaces for Virtual Environments and Teleoperator Systems*, pp. 465-471, Reno, Nev., March 2008. In this method, the error between the commanded and actual robot motion is used to estimate the force applied to the robot end-effector. Dynamic models of the robot are used to differentiate between forces from the environment (e.g. tissue) and forces from the internal mechanics of the robot (e.g. inertia and friction).

In another embodiment, tool-environment interaction data are visually obtained from the image system 114. The processor 116 instructs the manipulation tool 112 to exert a known amount of force on the environment. Based on the image from the image system 114, the processor 116 identifies contact between the manipulation tool 112 and the environment. The processor 116 can then determine the amount of displacement in the environment caused by the manipulation tool 112 based on visual analysis of the environment image or based on changes in position data of the manipulation tool 112. The tool-environment interaction data include the amount of displacement and the processor 116 calculates the stiffness estimates based on the amount of displacement. According to another embodiment, the tool-environment interaction sensor and visually determined tool-environment interaction data are both used by the surgical robot 100.

Figure 3:
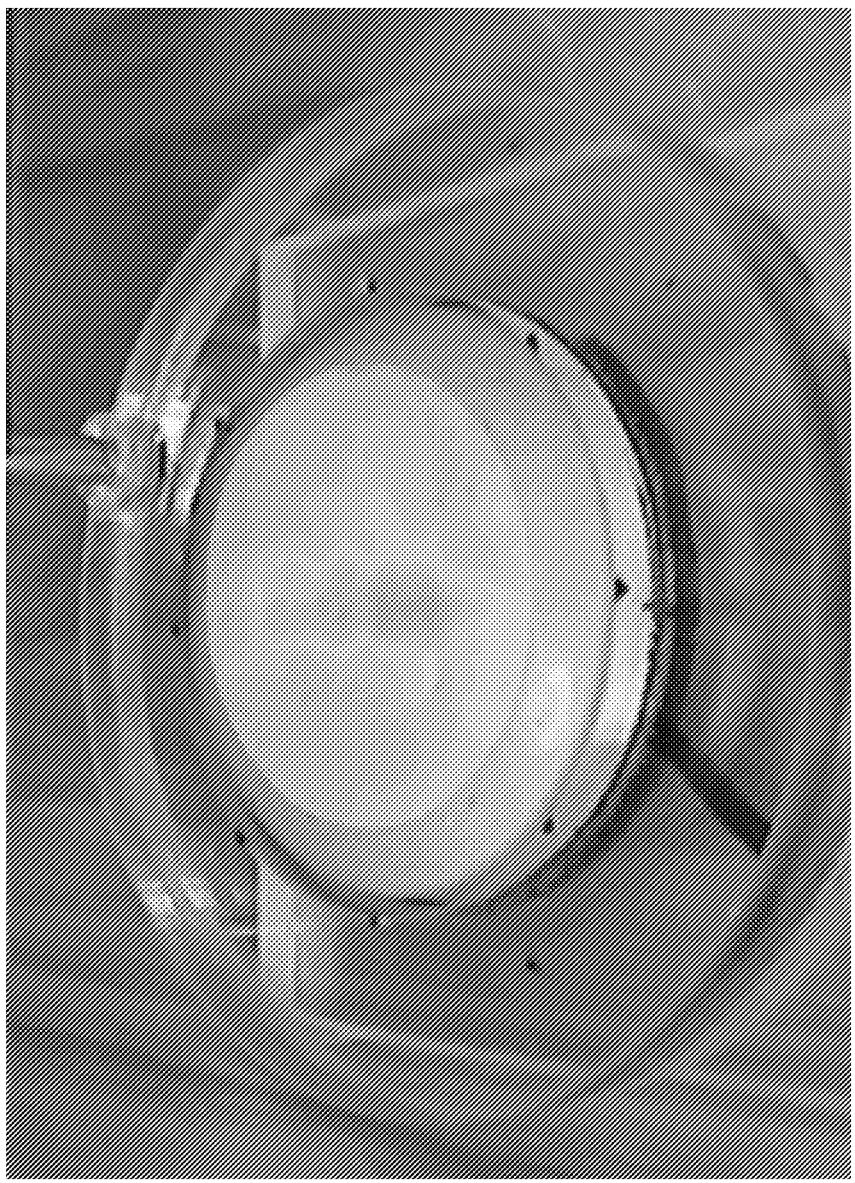
FIG. 3 is a diagram of a composite image showing a mechanical property map overlaid on an image of an environment according to an embodiment of the current invention.

FIG. 3 is a diagram of a composite image showing a stiffness map overlaid on an image of an environment according to an embodiment of the current invention. The processor 116 creates a stiffness map of the tissue from the stiffness estimates. The stiffness map is a graphical representation of the estimated stiffness of the tissue. In an embodiment, the stiffness map is a hue-saturation-luminance (HSL) representation. Hue corresponds to a stiffness value and saturation is calculated by a weighted Gaussian function. Based on the distance from a palpated point, the processor 116 defines a confidence level for the surrounding areas, which is interpreted as a saturation value. In an embodiment, when multiple confidence levels overlap in the same point, hue is blended to make a blended continuous colored map. The processor 116 sums confidence levels to increase reliability at the palpated point. In an embodiment, the processor 116 updates the stiffness map in real time as new data are gathered.

In an embodiment, the stiffness map is a three-dimensional map (a surface map embedded in three dimensions) and the processor 116 overlays the three-dimensional stiffness map on the environment image. The processor 116 receives a stereo view of an environment. The stereo view includes two images of the environment from the imaging system 114. Using the stereo view, the processor 116 determines the contours of the environment as shown in the stereo view. The processor 116 then creates the composite image so the three dimensional stiffness map corresponds to the contours of the environment.

Another embodiment of the current invention is directed to a data processing unit for use with a surgical robot. For example, the data processing unit may be similar to the processor 116 described with reference to the surgical robot in FIG. 1. The data processing unit has at least one input port adapted to receive an environment image from the surgical robot and to receive tool-environment interaction data from the surgical robot, an overlay component in communication with the at least one input port, and an output port in communication with the overlay component. The overlay component is adapted to calculate a mechanical property estimate for an area of an environment based on an environment model of tool-environment interaction data, create a composite image comprising a mechanical property map of the mechanical property estimate overlaid on the environment image, and output the composite image to the output port.

Another embodiment of the current invention is directed to a tangible machine readable storage medium that provides instructions, which when executed by a computing platform cause the computing platform to perform operations including a method including, according to an embodiment of the current invention, determining tool-environment interaction data from a palpation of an area of an environment, calculating a mechanical property estimate of the area of the environment based on the tool-environment interaction data, receiving an environment image, generating a composite image comprising a mechanical property map of the mechanical property estimate overlaid on the environment image, and outputting the composite image on a visual display.

EXAMPLES

Manual palpation of tissue and organs during a surgical procedure provides clinicians with valuable information for diagnosis and surgical planning. In present-day robot assisted minimally invasive surgery systems, lack of perceptible haptic feedback makes it challenging to detect a tumor in an organ or a calcified artery in heart tissue. This example presents an automated tissue property estimation method and a real-time graphical overlay that allow an operator to discriminate hard and soft tissues. We first evaluate experimentally the properties of an artificial tissue and compare seven possible mathematical tissue models. Self-validation as well as cross-validation confirm that the Hunt-Crossley model best describes the experimentally observed artificial tissue properties and is suitable for our purpose. Second, we present the development of a system in which the artificial tissue is palpated using a teleoperated surgical robot, and the stiffness of the Hunt-Crossly model is estimated in real time by recursive least squares. A real-time visual overlay representing tissue stiffness is created using a hue-saturation-luminance representation on a semi-transparent disc at the tissue surface. Hue depicts the stiffness at a palpated point and saturation is calculated based on distance from the point. A simple interpolation technique creates a continuous stiffness color map. In an experiment, the graphical overlay successfully shows the location of an artificial calcified artery hidden in artificial tissue.

In this work, we propose a real-time graphical overlay technique to display the location of hard objects hidden in soft materials, e.g. a calcified artery inside heart tissue. Our approach is to estimate the mechanical properties of tissue using recursive least squares (RLS) and simultaneously overlay a colored stiffness map on the surgeon's visual display. The graphical overlay clearly displays the location of a artificial calcified artery, as shown in FIG. 3. Another application is online detection of tumors. Our proposed technique may also be practical as an alternative to conventional force feedback, since simple force-sensing instruments designed specifically for palpation may be easier to develop than force sensing dexterous manipulation instruments.

Tissue Model

Human biological tissues are known to exhibit nonlinear properties and include inhomogeneous structures. For computational efficiency, however, many researchers assume a simple linear tissue model. In particular, a classical linear tissue model, such as a spring model or the Kelvin-Voigt model, is commonly employed (R. Corteso, J. Park, and O. Khatib, "Real-time adaptive control for haptic telemanipulation with kalman active observers," IEEE Transactions on Robotics, vol. 22, no. 5, pp. 987-999, 2006)(R. Corteso, W. Zarrad, P. Poignet, O. Company, and E. Dombre, "Haptic control design for robotic-assisted minimally invasive surgery," in IEEE International Conference on Intelligent Robots and Systems, pp. 454-459, 2006)(G. De Gersem, H. V. Brussel, and J. V. Sloten, "Enhanced haptic sensitivity for soft tissues using teleoperation with shaped impedance reflection," in World Haptics Conference (WHC) CD-ROM Proceedings, 2005)(S. Misra and A. M. Okamura, "Environment parameter estimation during bilateral telemanipulation," in 14th Symposium on Haptic Interfaces for Virtual Environments and Teleoperator Systems, pp. 301-307, 2006) (X. Wang, P. X. Liu, D. Wang, B. Chebbi, and M. Meng, "Design of bilateral teleoperators for soft environments with adaptive environmental impedance estimation," in IEEE International Conference on Robotics and Automation, pp. 1127-1132, 2005). Diolaiti et al. (N. Diolaiti, C. Melchiorri, and S. Stramigioli, "Contact impedance estimation for robotic systems," IEEE Transactions on Robotics, vol. 21, no. 5, pp. 925-935, 2005) used the Hunt-Crossley model (K. Hunt and F. Crossley, "Coefficient of restitution interpreted as damping in vibroimpact," ASME Journal of Applied Mechanics, vol. 42, no. 2, pp. 440-445, 1975). The nonlinear Hunt-Crossley model takes into account the energy loss during impact, which is observed in the Kelvin-Voigt model. While finite element modeling can provide superior tissue modeling, its computational complexity has limited its utility in real-time applications. Misra et al. (S. Misra, K. T. Ramesh, and A. M. Okamura, "Modeling of tool-tissue interactions for computer-based surgical simulation: A literature review," Presence: Teleoperators and Virtual Environments, vol. 17, no. 5, pp. 463-491, 2008) have reviewed the literature on the tool-tissue interaction methods.

Estimation Techniques

For online environment parameter estimation, there exist several methods, including RLS (X. Wang, P. X. Liu, D. Wang, B. Chebbi, and M. Meng, "Design of bilateral teleoperators for soft environments with adaptive environmental impedance estimation," in IEEE International Conference on Robotics and Automation, pp. 1127-1132, 2005)(N. Diolaiti, C. Melchiorri, and S. Stramigioli, "Contact impedance estimation for robotic systems," IEEE Transactions on Robotics, vol. 21, no. 5, pp. 925-935, 2005)(M. B. Colton and J. M. Hollerbach, "Identification of nonlinear passive devices for haptic simulations," in WHC '05: Proceedings of the First Joint Eurohaptics Conference and Symposium on Haptic Interfaces for Virtual Environment and Teleoperator Systems, (Washington, D.C., USA), pp. 363-368, IEEE Computer Society, 2005)(L. J. Love and W. J. Book, "Environment estimation for enhanced impedance control," in IEEE International Conference on Robotics and Automation, pp. 1854-1858, 1995), adaptive identification (S. Misra and A. M. Okamura, "Environment parameter estimation during bilateral telemanipulation," in 14th Symposium on Haptic Interfaces for Virtual Environments and Teleoperator Systems, pp. 301-307, 2006)(K. Hashtrudi-Zaad and S. E. Salcudean, "Adaptive transparent impedance reflecting teleoperation," in IEEE International Conferenceon Robotics and Automation, pp. 1369-1374, 1996)(H. Seraji and R. Colbaugh, "Force tracking in impedance control," IEEE Transactions on Robotics, vol. 16, no. 1, pp. 97-117, 1997)(S. K. Singh and D. O. Popa, "An analysis of some fundamental problems in adaptive control of force and impedance behavior: Theory and experiments," IEEE Transactions on Robotics and Automation, vol. 11, no. 6, pp. 912-921, 1995), Kalman filter approaches (R. Corteso, J. Park, and O. Khatib, "Real-time adaptive control for haptic telemanipulation with kalman active observers," IEEE Transactions on Robotics, vol. 22, no. 5, pp. 987-999, 2006)(R. Corteso, W. Zarrad, P. Poignet, O. Company, and E. Dombre, "Haptic control design for robotic-assisted minimally invasive surgery," in IEEE International Conference on Intelligent Robots and Systems, pp. 454-459, 2006)(G. De Gersem, H. V. Brussel, and J. V. Sloten, "Enhanced haptic sensitivity for soft tissues using teleoperation with shaped impedance reflection," in World Haptics Conference (WHC) CD-ROM Proceedings, 2005), and a multiestimator technique (T. Yamamoto, M. Bernhardt, A. Peer, M. Buss, and A. M. Okamura, "Multi-estimator technique for environment parameter estimation during telemanipulation," in *IEEE International Conference on Biomedical Robotics and Biomechatronics*, pp. 217-223, 2008). Erickson et al. (D. Erickson, M. Weber, and I. Sharf, "Contact stiffness and damping estimation for robotic systems," *The International Journal of Robotics Research*, vol. 22, no. 1, pp. 41-57, 2003) reviewed and compared four methods: RLS, indirect adaptive control, model-reference adaptive control, and a signal processing technique. They estimated environment stiffness and damping to improve force tracking and stability of impedance control for the application of robotic assembly operations. They concluded that indirect adaptive control, with persistent excitation, showed the best performance among the four schemes. Yamamoto et al. (T. Yamamoto, M. Bernhardt, A. Peer, M. Buss, and A. M. Okamura, "Multi-estimator technique for environment parameter estimation during telemanipulation," in *IEEE International Conference on Biomedical Robotics and Biomechatronics*, pp. 217-223, 2008) compared RLS, adaptive identification, and the multi-estimator technique to estimate unknown parameters of the Kelvin-Voigt model for surgical applications. They recommend RLS or the multi-estimator for online tissue parameter estimation.

Tissue Property Estimation

Some hard inclusions can be found using ultrasound, and prior work has examined intuitive visualization of laparoscopic ultrasound data using the da Vinci Surgical System (J. Leven, D. Burschka, R. Kumar, G. Zhang, S. Blumenkranz, X. Dai, M. Awad, G. D. Hager, M. Marohn, M. Choti, C. Hasser, and R. H. Taylor, "Davinci canvas: A telerobotic surgical system with integrated, robot-assisted, laparoscopic ultrasound capability," in *Medical Image Computing and Computer-Assisted Intervention (MICCAI)*, pp. 811-818, 2005). Elastography, which typically uses ultrasound and displays strain distributions in the soft tissues, is an effective method to detect tumors. The main disadvantage of elastography is that it is computationally expensive (J. Ophir, S. Alam, B. Garra, F. Kallel, E. Konofagou, T. Krouskop, C. Merritt, R. Righetti, R. Souchon, S. Srinivasan, and T. Varghese, "Elastography: Imaging the elastic properties of soft tissues with ultrasound," in *Journal of Medical Ultrasonics*, vol. 29, pp. 155-171, 2002). Some novel devices specialized for localization of tumors have been developed, e.g. Tactile Imaging (P. S. Wellman, E. P. Dalton, D. Krag, K. A. Kern, and R. D. Howe, "Tactile imaging of breast masses first clinical report," *Archives of Surgery*, vol. 136, pp. 204-208, 2001), Tactile Imaging System (A. P. Miller, W. J. Peine, J. S. Son, and Z. T. Hammoud, "Tactile imaging system for localizing lung nodules during video assisted thoracoscopic surgery," in *IEEE International Conference on Robotics and Automation*, pp. 2996-3001, 2007), Active Strobe Imager (M. Kaneko, C. Toya, and M. Okajima, "Active strobe imager for visualizing dynamic behavior of tumors," in *IEEE International Conference on Robotics and Automation*, pp. 3009-3014, 2007), PVDF-sensing grippers (J. Dargahi, S. Najarian, and R. Ramezanifard, "Graphical display of tactile sensing data with application in minimally invasive surgery," *Canadian Journal of Electrical and Computer Engineering*, vol. 32, no. 3, pp. 151-155, 2007), Tactile Sensing Instrument (A. L. Trejos, J. Jayender, M. T. Perri, M. D. Naish, R. V. Patel, and R. A. Malthaner, "Experimental evaluation of robot-assisted tactile sensing for minimally invasive surgery," in *IEEE International Conference on Biomedical Robotics and Biomechatronics*, pp. 971-976, 2008), and Air-Cushion Force Sensitive Probe (K. Althoefer, D. Zbyszewski, H. Liu, P. Puangmali, L. Seneviratne, B. Challacombe, P. Dasgupta, and D. Murphy, "Air-cushion force sensitive probe for soft tissue investigation during minimally invasive surgery," in *IEEE Conference on Sensors*, pp. 827-830, 2008), but none have been tested in RMIS systems yet.

This example describes (1) validation of a mathematical artificial artificial tissue model and (2) use of the model and teleoperated robot to create a real-time graphical overlay to represent tissue stiffness, thus enabling an operator to identify an invisible hard inclusion inside a soft material.

To choose an accurate mathematical model of the artificial tissue, we analyzed experimental tool-environment interaction data and compared seven candidate models. By post processing using the least-squares method, we evaluated the model accuracy based on the force estimation error in both self-validation and cross-validation. The Hunt-Crossley model was chosen because of its accuracy and a stiffness term that distinguishes hard objects from the soft materials. Since in the long term we aim to model real tissues, which are inhomogeneous and complex, both validations are useful to mathematically approximate tissue dynamic behavior.

We have also developed an online graphical overlay technique that displays stiffness distribution based on estimated tissue properties. A hue-saturation-luminance (HSL) representation is used to overlay a semi-transparent colored stiffness map on the environment image. Hue corresponds to a stiffness value and saturation is calculated by a weighted Gaussian function. Based on the distance from a palpated point, we define a confidence level for the surrounding areas, which is interpreted as a saturation value. When multiple confidence levels overlap in the same point, hue is blended to make a continuous colored map. Also, the confidence levels are summed to increase reliability at the palpated point. This procedure is repeated in real time as new data are added. As a result, we have achieved a semi-transparent, colored stiffness map that displays the location of a hard inclusion, without obscuring the surgeon's view of the tissue or surgical instrument.

Tissue Model Selection

Although it is nearly impossible to find a perfect mathematical model of a real or artificial tissue, there may be one that can approximate tissue dynamic behavior. Seven possible models are considered, however other models can be used. From tool-environment interaction data, we compare all of the models and evaluate the accuracy based on force estimation error.

A. Artificial Tissue

The artificial tissue heart model is made from Ecoflex 0030 (part A and B), silicone thinner, and silc pigment (Smooth-on Inc., Easton, Pa., USA) mixed in a 24:24:12:1 ratio. To simulate a calcified artery, a coffee stir straw is embedded in the artificial tissue. Our surgeon collaborator tested the potential models to make a realistic choice of artificial tissue samples. The diameter and thickness of a artificial tissue heart model are approximately 60 mm and 18.5 mm, respectively. A coffee stir straw with diameter of 4 mm is embedded at the depth of 5 mm from the surface.

B. Model Candidates

We compare the seven models listed in Table I. $\hat{f}$ is an estimated interaction force between the tool and the environment, and x, $\dot{x}$ and $\ddot{x}$ are position, velocity, and acceleration of the tool, respectively. The remaining terms, if, $\hat{x}_0$, $\hat{k}$, $\hat{b}$, $\hat{m}$, $\hat{\lambda}$, $\hat{n}$, $\hat{\alpha}_i$, and $\beta$, are unknown parameters to be estimated.

TABLE I

SEVEN ENVIRONMENT MODELS AND COMPARISON OF MEAN AND
STANDARD DEVIATION OF FORCE ESTIMATION ERROR

| | | Self-Validation | | | | Cross-Validation | | | |
| | | Soft Tissue | | Calcified Artery | | Soft Tissue | | Calcified Artery | |
| # Model Name | Equation of Model | Mean | Std | Mean | Std | Mean | Std | Mean | Std |
| --- | --- | --- | --- | --- | --- | --- | --- | --- | --- |
| 1 Kelvin-Voigt | $\hat{f} = \hat{x}_0 + \hat{k}x + \hat{b}\dot{x}$ | 0.149 | 0.120 | 0.478 | 0.389 | 0.375 | 0.163 | 0.645 | 0.465 |
| 2 mass-damper-spring | $\hat{f} = \hat{x}_0 + \hat{k}x + \hat{b}\dot{x} + \hat{m}\ddot{x}$ | 0.135 | 0.108 | 0.445 | 0.352 | 0.364 | 0.151 | 0.637 | 0.438 |
| 3 Hunt-Crossley | $\hat{f} = \hat{x}_0 + \hat{k}x^n + \hat{\lambda}x^n\dot{x}$ | 0.078 | 0.081 | 0.245 | 0.235 | 0.369 | 0.104 | 0.431 | 0.271 |
| 4 2nd order polynomial | $\hat{f} = \hat{\alpha}_0 + \hat{\alpha}_1 x + \hat{\alpha}_2 x^2$ | 0.095 | 0.104 | 0.291 | 0.275 | 0.369 | 0.112 | 0.439 | 0.288 |
| 5 3rd order polynomial | $\hat{f} = \hat{\alpha}_0 + \hat{\alpha}_1 x + \hat{\alpha}_2 x^2 + \hat{\alpha}_3 x^3$ | 0.091 | 0.102 | 0.256 | 0.285 | 0.392 | 0.140 | 0.448 | 0.323 |
| 6 4th order polynomial | $\hat{f} = \hat{\alpha}_0 + \hat{\alpha}_1 x + \hat{\alpha}_2 x^2 + \hat{\alpha}_3 x^3 + \hat{\alpha}_4 x^4$ | 0.090 | 0.102 | 0.232 | 0.271 | 0.406 | 0.170 | 0.514 | 0.342 |
| 7 2nd order polynomial + velocity-dependent | $\hat{f} = \hat{\alpha}_0 + \hat{\alpha}_1 x + \hat{\alpha}_2 x^2 + \hat{\beta}\dot{x}$ | 0.074 | 0.070 | 0.234 | 0.198 | 0.391 | 0.134 | 0.464 | 0.322 |

C. Tool-Environment Interaction Data

We first conducted a preliminary palpation experiment to obtain the tool-environment interaction data. An instrument extension with a plastic disc, FIG. 2A, is attached at the tip of an instrument. The diameter of the artificial calcified artery is 4 mm, and the disc is 10 mm in diameter. Due to the size and the flatness of the disc, the tool does not slide off the artery when force is applied. The instrument is mounted on a patient-side manipulator of our da Vinci Surgical System, as explained later. As shown in FIG. 2B, the artificial heart tissue was placed on a plastic base mounted on a Nano17 transducer (ATI Industrial Automation, Apex, N.C., USA).

There were five trials each for the soft tissue and calcified artery. During a trial, the instrument was restricted to up and down motions, so the system had one degree of freedom in this preliminary experiment. Probed locations were different trial by trial to obtain a wide range of data. The patient-side manipulator was teleoperated by a master manipulator and a user received haptic feedback based on a position-position controller (M. Mahvash and A. M. Okamura, "Enhancing transparency of a position-exchange teleoperator," in *Second Joint Eurohaptics Conference and Symposium on Haptic Interfaces for Virtual Environment and Teleoperator Systems* (*World Haptics*), pp. 470-475, 2007). Position, velocity, and acceleration of the tool and the applied forces to the artificial tissue were recorded.

D. Model Validation

We post-processed the data for each trial and the unknown parameters and interaction force were estimated for each model. To verify model accuracy, batch post-processing was employed. Models 1, 2, and 4-7 are linear in the unknown parameters, and the linear least-squares method was used.

$$f(t) = \varphi^T(t)\theta \qquad (1)$$

$$\theta = (X^T X)^{-1} X^T Y \qquad (2)$$

where $$\begin{cases} X = [\varphi_1, \varphi_2, \ldots, \varphi_n]^T \\ Y = [f_1, f_2, \ldots, f_n]^T. \end{cases}$$

In (1), $\varphi$ is a regression vector including known parameters, $\theta$ is an unknown parameter vector, and in (2) the subscript k ($1 \leq k \leq n$) denotes $t=kT$ with sampling time T.

Model 3 is nonlinear in unknown parameters because of the exponent $\hat{n}$. We used nonlinear least squares with the Gauss-Newton method. Let us define $$\hat{f} = g(\phi, \theta) = \hat{\chi}_0 + \hat{k}\chi^{\hat{n}} + \hat{\lambda}\chi^{\hat{n}}\dot{\chi}, \qquad (3)$$

where $\phi = [\chi, \dot{\chi}]^T$ and $\theta = [\hat{\chi}_0, \hat{k}, \hat{\lambda}, \hat{n}]^T$. At the k-th iteration, the estimated parameters are $$\theta^{k+1} = \theta^k + \Delta\theta, \qquad (4)$$

$$\Delta\theta = (J^T J)^{-1} J^T \Delta Y, \qquad (5)$$

where $$\begin{cases} J_{ij} = \left.\dfrac{\partial g(\varphi, \theta)}{\partial \theta_j}\right|_{\varphi_i, \theta^k} \\ \Delta Y = [\Delta y_1, \Delta y_2, \ldots, \Delta y_n]^T \\ \Delta y_i = f_i - g(\varphi_i, \theta). \end{cases}$$

Nonlinear least squares has no closed-form solution and requires initial values for the unknown parameters. We set $\theta^0 = [0, 5, 0.3, 1.5]^T$ by trial and error to avoid local minima sometimes observed when $\theta^0$ is a zero vector). Note that the units of force and position are Newton and centimeter, respectively, throughout this document. The iteration number k started from 0 and increased until the norm of the increment parameter vector $\Delta\theta$ was less than 0.001.

1) Self-Validation: The force estimation error is defined as $$\Delta y_i = |f_i - \hat{f}_i|.$$

The mean and standard deviation of the force estimation error for each model are summarized in Table I. Since there are five sets of the palpation data for the soft tissue and calcified artery, the mean and standard deviation are averaged. The lower the mean and standard deviation of the force estimation errors a model yields, the more accurate it is. Models 3, 5, 6, and 7 therefore seem to characterize the dynamics of both soft tissue and calcified artery well, while Models 1, 2, and 4 do not. FIG. 4 shows sample plots of interaction data of the tool and the environment.

Figures 4A, 4B:
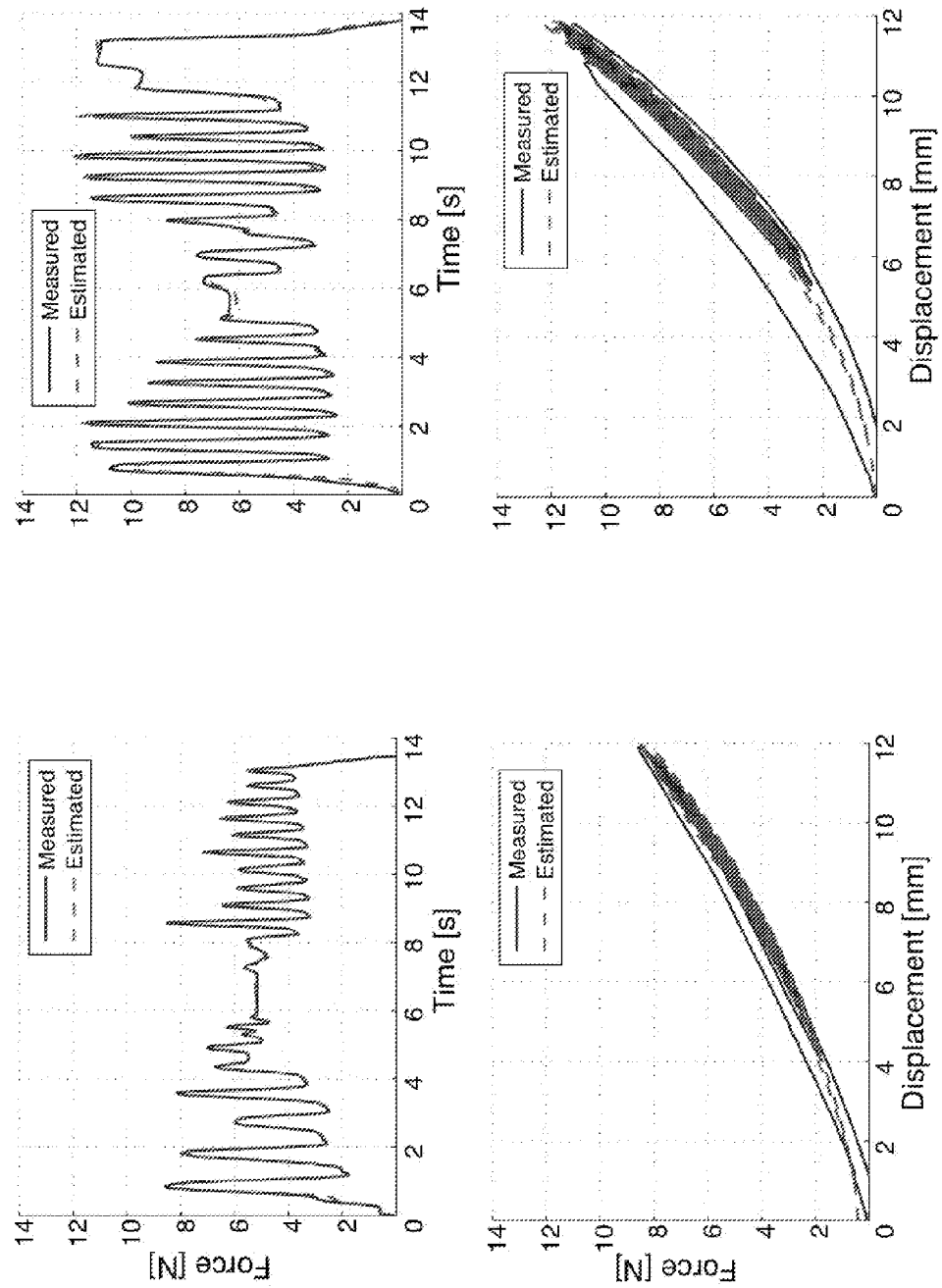
FIGS. 4A and 4B show sample plots of (4A) artificial soft tissue and (4B) artificial calcified artery showing (Top) force vs. elapsed time and (Bottom) force vs. displacement when using a mass-damper-spring model to calculate estimated force according to an embodiment of the current invention.

FIGS. 4A and 4B show sample plots of (4A) soft tissue and (4B) calcified artery showing (Top) force vs. elapsed time and (Bottom) force vs. displacement when using a mass-damper-spring model to calculate estimated force.

2) Cross-Validation: From self-validation, we obtained one set of estimated parameters from a single trial for each model. In cross-validation, those parameters were used to calculate estimated forces for the other trials. For instance, an estimated parameter vector from trial 1 was used to calculate force for trials 1-5. This was done for every trial. Therefore, $5^2=25$ force estimation errors were calculated for each model. In Table I, the mean and standard deviation of the force estimation error for each model are summarized. FIG. 5 shows a comparison of measured and recreated force, based on one of the trial data for the calcified artery, for Models 1 and 3.

Figures 5A, 5B:
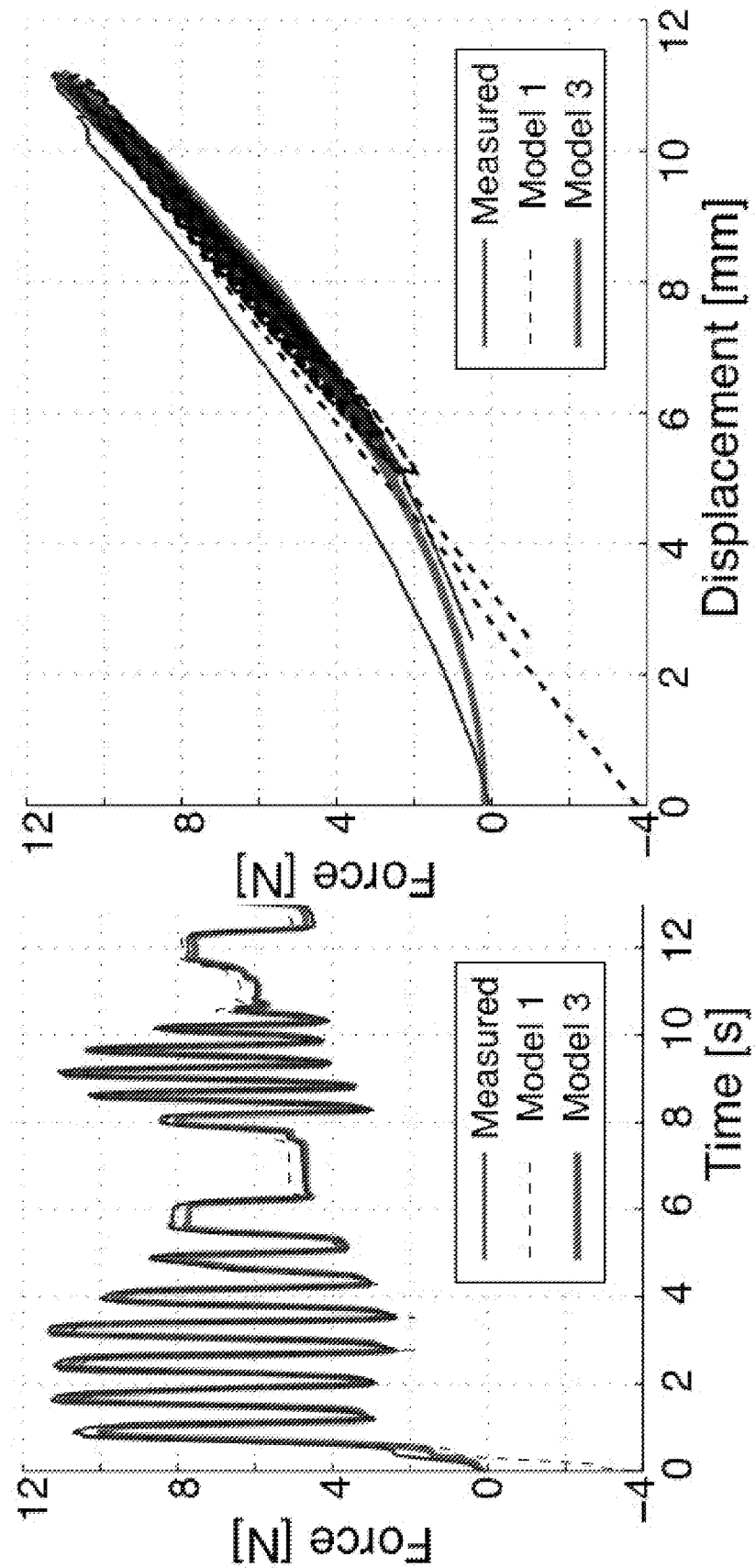
FIGS. 5A and 5B show force plots of (5A) force vs. elapsed time and (5B) force vs. displacement from one of the artificial calcified artery according to an embodiment of the current invention.

FIGS. 5A and 5B show force plots of (5A) force vs. elapsed time and (5B) force vs. displacement from one of the calcified artery.

3) Analysis of Both Validations: In self-validation, the higher the order of a polynomial function model is, the lower errors the model yields. Models 1, 2, and 6 are inferior to the others. Model 6 is good in self-validation but not in cross-validation. From both validation tests, either Model 3 or 7 is appropriate for our artificial tissue heart model with the calcified artery. For our purpose, however, Model 3 is a better choice. To discriminate the hard inclusions from the soft surrounding material, we would like to identify a physically meaningful difference. Table II summarizes the estimated parameters of Models 3 and 7. While $\hat{k}$ of Model 3 shows a consistent difference between the artificial tissue and the artificial calcified artery, any parameters of Model 7 do not show a consistent difference. Therefore, we chose Model 3, the Hunt-Crossley model.

TABLE II

COMPARISON OF ESTIMATED PARAMETERS OF MODELS 3 AND 7

| | Trial Number | Model 3 | | | | Model 7 | | | |
|---|---|---|---|---|---|---|---|---|---|
| | | $\hat{x}_0$ | $\hat{k}$ | $\hat{\lambda}$ | $\hat{n}$ | $\hat{a}_0$ | $\hat{a}_1$ | $\hat{a}_2$ | $\hat{\beta}$ |
| Soft Tissue | 1 | 0.708 | 5.518 | 0.090 | 1.679 | 0.155 | 3.697 | 4.588 | 0.258 |
| | 2 | 0.668 | 5.544 | 0.115 | 1.570 | 0.519 | 0.427 | 6.687 | 0.286 |
| | 3 | 0.416 | 5.741 | 0.198 | 1.391 | 0.028 | 5.679 | 2.461 | 0.202 |
| | 4 | 0.327 | 4.960 | 0.134 | 1.686 | 0.036 | 4.867 | 2.581 | 0.208 |
| | 5 | 1.025 | 5.984 | 0.211 | 1.587 | 0.373 | 3.302 | 5.654 | 0.306 |
| Calcified Artery | 1 | 0.178 | 8.687 | 0.200 | 1.849 | 0.352 | 3.432 | 6.984 | 0.294 |
| | 2 | 0.249 | 8.490 | 0.272 | 1.934 | 0.210 | 4.936 | 5.701 | 0.228 |
| | 3 | 0.702 | 10.412 | 0.411 | 1.613 | 0.374 | 5.374 | 6.181 | 0.205 |
| | 4 | 0.458 | 9.960 | 0.380 | 1.622 | 0.720 | 5.087 | 6.533 | 0.259 |
| | 5 | 0.770 | 10.293 | 0.491 | 1.750 | 0.328 | 5.963 | 5.174 | 0.418 |

System Design

A. Teleoperation System

Figure 6:
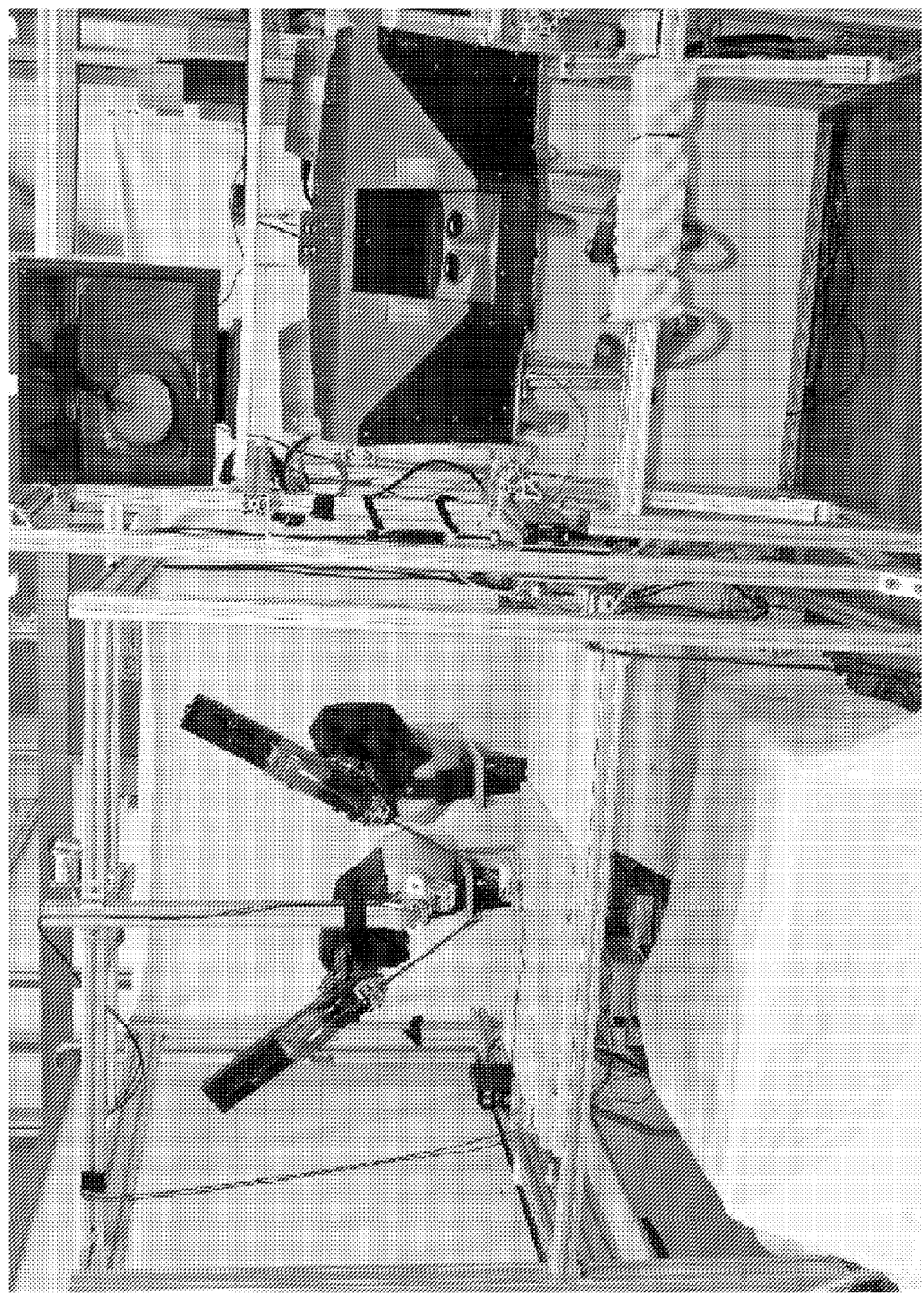
FIG. 6 shows a schematic illustration of a custom version of the da Vinci Surgical System where the master manipulators and the 3D vision display system are located on the right, and the patient-side manipulators and a stereo camera are on the left according to an embodiment of the current invention.

FIG. 6 shows a schematic illustration of a custom version of the da Vinci Surgical System where the master manipulators and the 3D vision display system are located on the right, and the patient-side manipulators and a stereo camera are on the left.

Our custom version of the da Vinci Surgical System, shown in FIG. 6, includes three components: master manipulators, 3D vision system, and patient-side manipulators. The hardware is provided by Intuitive Surgical, Inc., and a custom control system has been developed at the Johns Hopkins University to achieve bilateral telemanipulation. More details about the teleoperation system and the control architecture are summarized in (M. Mahvash, J. Gwilliam, R. Agarwal, B. Vagvolgyi, L.-M. Su, D. D. Yuh, and A. M. Okamura, "Force-feedback surgical teleoperator: Controller design and palpation experiments," in 16th Symposium on Haptic Interfaces for Virtual Environments and Teleoperator Systems, pp. 465-471, 2008). Although the user received force feedback based on the position-position controller during an experiment, all we need for estimation are tool-environment interaction data.

B. Estimation Technique and Initial Setup

We employed RLS to estimate unknown parameters of the model in real time. Due to fast parameter convergence and accuracy of RLS, even one palpation may be enough for the unknown parameters to converge (T. Yamamoto, M. Bernhardt, A. Peer, M. Buss, and A. M. Okamura, "Multi-estimator technique for environment parameter estimation during telemanipulation," in IEEE International Conference on Biomedical Robotics and Biomechatronics, pp. 217-223, 2008). Since the Hunt-Crossley model is nonlinear, the unknown parameters are decoupled so that two linear RLS estimators can be used (N. Diolaiti, C. Melchiorri, and S. Stramigioli, "Contact impedance estimation for robotic systems," IEEE Transactions on Robotics, vol. 21, no. 5, pp. 925-935, 2005): $\Gamma_1$ estimates $\hat{x}_0$, $\hat{k}$, and $\hat{\lambda}$, and $\Gamma_2$ estimates the exponent $\hat{n}$. Both estimators are interconnected via feedback. Note that we added the position offset $\hat{x}_0$ to the original method presented in N. Diolaiti, C. Melchiorri, and S. Stramigioli, "Contact impedance estimation for robotic systems," IEEE Transactions on Robotics, vol. 21, no. 5, pp. 925-935, 2005. At each time step, the parameter vector is updated as:

$$\hat{\theta}_n = \hat{\theta}_{n-1} + L_n[y_n - \varphi_n^T \hat{\theta}_{n-1}], \tag{7}$$

where (8)

$$\begin{cases} L_n = P_{n-1}\varphi_n(\beta + \varphi_n^T P_{n-1}\varphi_n)^{-1} \\ P_n = \beta^{-1}[I - L_n\varphi_n^T]P_{n-1}, \end{cases}$$

where $\beta (0 < \beta \leq 1)$ is a forgetting factor. Specifically, $$\Gamma_1: y = f, \varphi = [1, x^{\hat{n}}, x^{\hat{n}}\dot{x}]^T, \theta = [\hat{x}_0, \hat{k}, \hat{\lambda}]^T, \tag{9}$$

$$\Gamma_2: y = \log\frac{f - \hat{x}_0}{\hat{k} + \hat{\lambda}\dot{x}}, \varphi = \log x, \theta = \hat{n}.$$

Our initial guess is the same as that for the model validation, i.e. $\theta_0 = [0, 5, 0.3, 1.5]$. The initial covariance matrix $P_0$ is an identity matrix multiplied by 100. Since we have verified that the model is accurate, the forgetting factor is not necessary. Therefore, we chose $\beta = 1$. To start and end the estimation for palpation at each location, we set a force threshold to detect contact between the palpation tool and the artificial tissue. By considering noise level from the force sensor, if the product of previous and current force along the vertical axis is bigger than 0.002 $N^2$, the tool is considered to have made contact with the environment. When contact is detected, the estimation automatically starts and the stiffness is overlaid in the monitor as described in the following section. To avoid the effects of tremor of the tool on the visual overlay, the position of the palpated point is fixed at the contact. It is released when the tool is away from the tissue. The parameters of RLS are all initialized at every release.

C. Stereo Camera System

The coordinates between the stereo camera and the patient-side manipulator were calibrated by an AX=XB calibration using a custom-made calibration device. The result of this calibration is the transformation frame between the Cartesian manipulator tool tip coordinates and the Cartesian camera frame (the camera frame is centered halfway between the two cameras). In the other calibration step, we calibrated the transformation between the camera frame and the overlay (environment) platform frame using a rigid registration between the rigid body defined by the platform and the 3D point cloud reconstructed from the stereo video.

During the experiments, to place the overlay image precisely, we first transformed the tool-tip position from the robot coordinates to the camera coordinates, then from the camera coordinates to the platform coordinates. Since the platform texture is parallel to the x-z plane, we could easily project the transformed tool-tip position onto the texture surface.

D. Visual Overlay Method

A color map using the HSL representation is overlaid on the stereo camera images to display the stiffness of the palpated points. Since the data are analyzed in real time, while the artificial tissue is being palpated, the estimated stiffness and the palpated position data are simultaneously transferred to a vision computer and displayed by a semitransparent color graphical overlay at a rate of 30 Hz. With transparency of 50%, the camera images are clearly visible behind the overlaid image. Thus, the colored stiffness map does not obscure the user's view of the tool or the surface features of the artificial tissue.

Hue corresponds to stiffness, and the color ranges from green, passing through yellow, to red. Based on the preliminary palpation task, we defined the range of stiffness k from 6 to 10. Saturation value is calculated based on a Gaussian function. By using a weighted probability distribution function of Gaussian distribution, we define the confidence level as $h(x)=\exp((x-\mu)^2/\sigma)$, ranging from 0 to 1. x and $\mu$ are elements of a vector such that the term $(x-\mu)^2$ is squared distance between the center of the palpated point and the surrounding regions. The standard deviation $\sigma$ was chosen such that the size of an overlaid circle corresponds to that of the palpation disc.

Figure 7A:
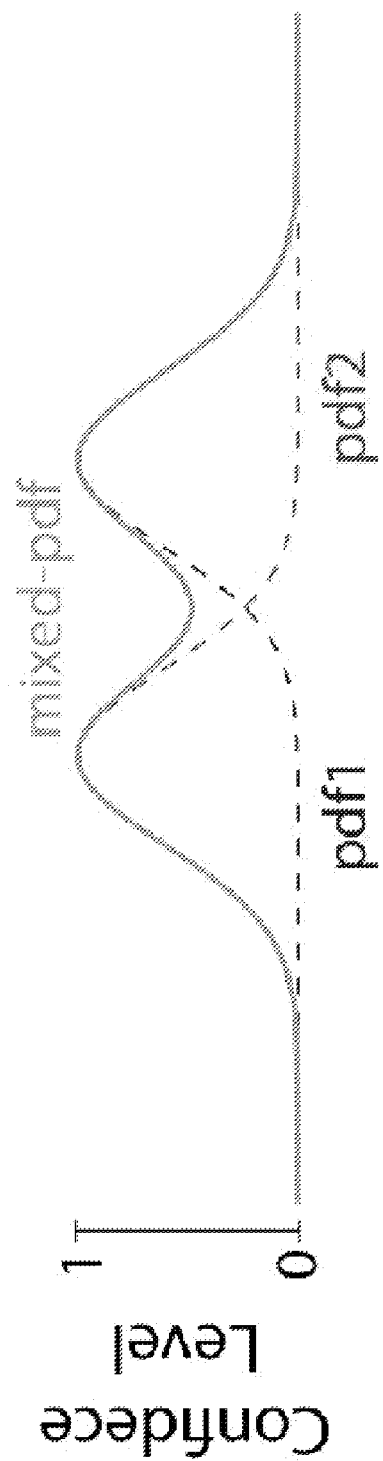
FIGS. 7A and 7B show plots of (7A) confidence level when summing overlapping probability density functions and (7B) hues indicating changes in stiffness and saturations indicating confidence level according to an embodiment of the current invention.
Figure 7B:
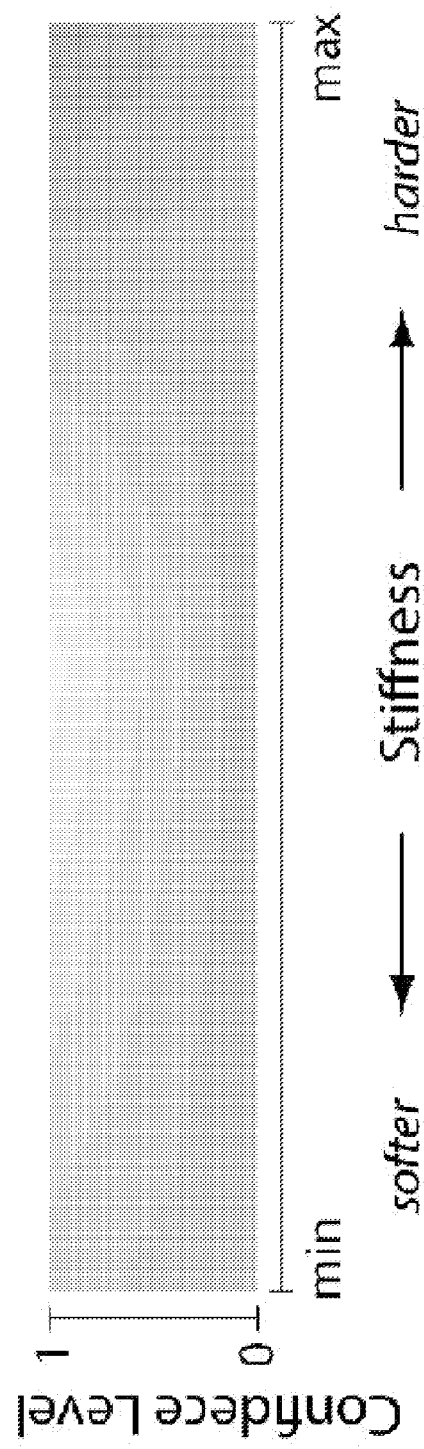

FIGS. 7A and 7B show plots of (7A) confidence level when summing overlapping probability density functions and (7B) hue indicating changes in stiffness and saturation indicating confidence level.

A simple summation interpolation technique is used when two or more probability density functions overlap, as shown in FIG. 7A. If the sum is more than 1, it is cut off to 1. Luminance is 0.5 for all pixels to show the overlay in color. FIG. 7B shows the HSL bar we used in our system.

EXPERIMENTAL RESULTS

Figure 8A:
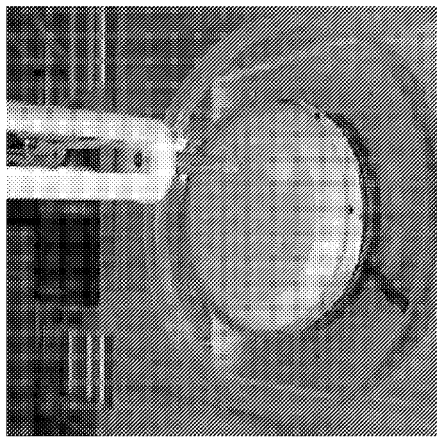
FIG. 8A-8D are diagrams of composite images as the stiffness map of the underlying environment shown in the image is developed according to an embodiment of the current invention.
Figure 8B:
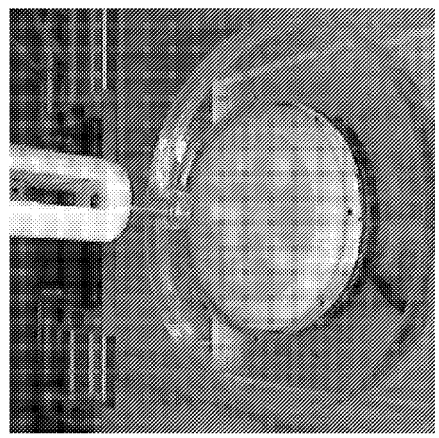
Figure 8C:
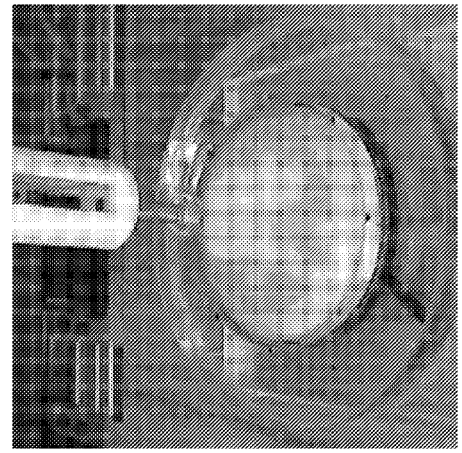
Figure 8D:
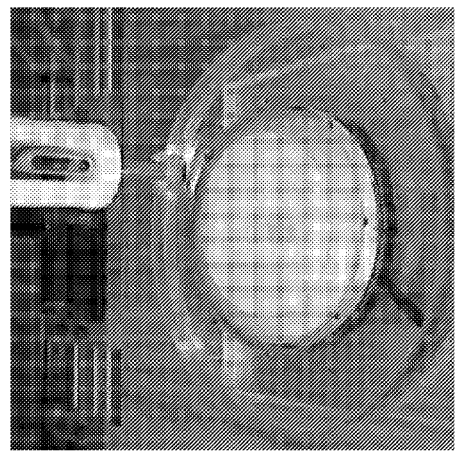

FIG. 8A-8D are diagrams of composite images as the stiffness map of the underlying environment shown in the image is developed. FIG. 8 shows four pictures taken during a trial. As soon as contact between the tool and artificial tissue was detected, a semi-transparent colored circle was displayed on the stereo monitor of the surgeon's console. Each palpation at a single location lasted approximately half a second. FIG. 8A shows the result of the first palpation. In FIG. 8B, there are several circles displayed due to random palpation. When a current palpated area is close to others palpated before, the interpolation technique is used to blend the color and sum the confidence level. One of the intermediate results is shown in FIG. 8C. At this point, one can see a red area that vertically goes through the center. When the entire surface of the artificial tissue has been palpated, the red region is very distinct, as shown in FIG. 8D. Due to the size of the overlaid circle, whose diameter is more than twice the diameter of the artificial calcified artery, the width of the red region is approximately 8 mm while the actual width of the artificial calcified artery is 4 mm. However, for example, once the approximate location is identified, the size of the overlaid circle or the standard deviation of the Gaussian could be reduced to detect more precise size and location of the artificial calcified artery.

This example presents the use of a teleoperated surgical robot for online estimation of tissue properties, and identification of a hard object hidden in soft materials using a colored stiffness map overlaid on the surgeon's monitor. Among seven potential mathematical models for a artificial tissue, we choose the Hunt-Crossley model, which provides the lowest force estimation errors in both self-validation and cross-validation and shows a consistent difference between the artificial tissue and the artificial calcified artery. Recursive least squares is used to estimate the unknown parameters of the Hunt-Crossley model. The estimated stiffness is transmitted to a vision computer to create a graphical overlay using the hue-saturation-luminance map. The hue of the graphical overlay is determined by the stiffness. For saturation, a confidence level is defined by a weighted Gaussian function, based on distance from a palpated point. To create a continuously blended colored map, a simple interpolation technique is used. By probing over the surface of an artificial heart tissue, we successfully acquire a color map showing the location of an artificial calcified artery.

We can replace the force sensor by an existing force estimation technique, e.g. (P. Hacksel and S. Salcudean, "Estimation of environment forces and rigid-body velocities using observers," in *IEEE International Conference on Robotics and Automation*, pp. 931-936, 1994), so that our method can be implemented without adding any devices to the commercial robot. Alternatively, a specialized force sensing palpation tool can be used. Visualization of the surgical instrument can be improved by segmenting the instrument in the image and placing it over the semi-transparent display of tissue properties. As a path to clinical application, the stiffness map can follow the contours of any tissue surface, using computer vision, pre-operative images, or a combination of the two. Such a system should be tested on biological tissues. Finally, the acquired tissue properties can be used in automated diagnosis and surgical planning, extracted for the creation of realistic patient-specific surgical simulators, and used to make improvements to the transparency of a bilateral teleoperator.

The current invention is not limited to the specific embodiments of the invention illustrated herein by way of example, but is defined by the claims. One of ordinary skill in the art would recognize that various modifications and alternatives to the examples discussed herein are possible without departing from the scope and general concepts of this invention.

We claim:
1. A surgical robot, comprising:
   an imaging system comprising at least one camera;
   a processor in communication with said imaging system;
   a manipulation system in communication with said processor; and
   a visual display in communication with said processor, wherein said processor is operable to:
calculate a mechanical property estimate for an area of an environment based on an environment model of tool-environment interaction data;
create a composite image comprising a mechanical property map of the mechanical property estimate overlaid on an environment image from said at least one camera; and
output the composite image on said visual display.

2. The surgical robot of claim 1, wherein said processor is operable to create the mechanical property map based on translation of the mechanical property estimate to the environment image.

3. The surgical robot of claim 1, wherein an area of said mechanical property map overlaid on the environment image corresponds to the area of the environment shown overlaid by said area of said mechanical property map in the environment image.

4. The surgical robot of claim 3, wherein said mechanical property map comprises a hue-saturation-luminence colored mechanical property map, wherein the hue corresponds to a mechanical property value for an area of said mechanical property map and the saturation corresponds to a confidence level for the area of said mechanical property map.

5. The surgical robot of claim 1, wherein said mechanical property map comprises a blended mechanical property map.

6. The surgical robot of claim 1, wherein said manipulation system further comprises a tool-environment interaction sensor.

7. The surgical robot of claim 6, wherein said tool-environment interaction sensor comprises a force sensor, wherein said tool-environment interaction data comprise an amount of force applied by said manipulation system to the environment.

8. The surgical robot of claim 1, wherein said tool-environment interaction data comprise an amount of displacement in the environment caused by said manipulation system.

9. The surgical robot of claim 1, wherein said processor is further operable to create the composite image in real time.

10. The surgical robot of claim 1, wherein said environment model comprises a linear or nonlinear equation using the mechanical property of the environment to relate force and movement variables.

11. The surgical robot of claim 1, wherein said processor is further operable to apply an algorithm to estimate the mechanical property based on the environment model and said tool-environment interaction data.

12. The surgical robot of claim 1, wherein said mechanical property map comprises a surface mechanical property map embedded in three-dimensional space.

13. The surgical robot of claim 1, wherein said environment comprises at least one of tissue or an organ.

14. The surgical robot of claim 1, wherein said mechanical property comprises stiffness.

15. A data processing unit for use with a surgical robot, comprising:
at least one input port adapted to receive an environment image from the surgical robot and to receive tool-environment interaction data from the surgical robot;
an overlay component in communication with said at least one input port; and
an output port in communication with said overlay component,
wherein said overlay component is adapted to calculate a mechanical property estimate for an area of an environment based on an environment model of tool-environment interaction data, create a composite image comprising a mechanical property map of the mechanical property estimate overlaid on the environment image, and output the composite image to said output port.

16. The data processing unit of claim 15, wherein said overlay component is operable to create the mechanical property map based on translation of the mechanical property estimate to the environment image.

17. The data processing unit of claim 15, wherein an area of said mechanical property map overlaid on the environment image corresponds to the area of the environment shown overlaid by said area of said mechanical property map in the environment image.

18. The data processing unit of claim 17, wherein said mechanical property map comprises a hue-saturation-luminesce colored mechanical property map, wherein the hue corresponds to a mechanical property value for an area of said mechanical property map and the saturation corresponds to a confidence level for the area of said mechanical property map.

19. The data processing unit of claim 15, wherein said mechanical property map comprises a blended mechanical property map.

20. The data processing unit of claim 15, wherein said tool-environment interaction data comprise an amount of force applied by a manipulation system to the environment.

21. The data processing unit of claim 15, wherein said tool-environment interaction data comprises an amount of displacement in the environment caused by a manipulation system.

22. The data processing unit of claim 15, wherein said overlay component is further adapted to create the composite image in real time.

23. The data processing unit of claim 15, wherein said environment model comprises a linear or nonlinear equation using the mechanical property of the environment to relate force and movement variables.

24. The data processing unit of claim 15, wherein said overlay component is further adapted to apply an algorithm to estimate the mechanical property using the environment model and said tool-environment interaction data.

25. The data processing unit of claim 15, wherein said mechanical property map comprises a 3-D mechanical property map.

26. The data processing unit of claim 15, wherein said environment comprises at least one of tissue or an organ.

27. The data processing unit of claim 15, wherein said mechanical property comprises stiffness.

28. A tangible machine readable storage medium that provides instructions, which when executed by a computing platform, cause said computing platform to perform operations comprising a method comprising:
determining tool-environment interaction data from a palpation of an area of an environment;
calculating a mechanical property estimate of the area of the environment based on the tool-environment interaction data;
receiving an environment image;
generating a composite image comprising a mechanical property map of the mechanical property estimate overlaid on the environment; and
outputting the composite image on a visual display.

* * * * *